(12) United States Patent
Zhao

(10) Patent No.: US 6,372,489 B1
(45) Date of Patent: Apr. 16, 2002

(54) METHOD AND MODEL FOR HAIR PIGMENTATION

(75) Inventor: Ming Zhao, San Diego, CA (US)

(73) Assignee: AntiCancer, Inc., San Diego, CA (US)

( * ) Notice: Subject to any disclaimer, the term of this patent is extended or adjusted under 35 U.S.C. 154(b) by 0 days.

(21) Appl. No.: 09/427,700

(22) Filed: Oct. 27, 1999

Related U.S. Application Data

(60) Provisional application No. 60/105,725, filed on Oct. 27, 1998.

(51) Int. Cl.[7] .......................... C12N 5/00; C12N 15/63; C07H 21/04; C12P 21/06
(52) U.S. Cl. .................... 435/325; 536/23.7; 536/24.1; 536/23.2; 435/320.1; 435/69.1; 435/455
(58) Field of Search .......................... 514/44; 435/320.1, 435/691, 325, 455, 456, 458; 536/23.1, 23.2, 23.7, 24.1

(56) References Cited

U.S. PATENT DOCUMENTS 5,753,263 A 5/1998 Lishko et al. ............... 424/450

FOREIGN PATENT DOCUMENTS

| WO | WO 88 02372 | 4/1988 |
|---|---|---|
| WO | WO 94 22468 | 10/1994 |
| WO | WO 95 13386 | 5/1995 |
| WO | WO 96 40959 | 12/1996 |
| WO | WO 98 46208 | 10/1998 |

OTHER PUBLICATIONS

Pizzato, M. et al. Production and characterization of a bicistronic Moloney–based retroviral vector expressing human interleukin 2 and herpes simplex virus thymidine kinase for gene therapy of cancer. Gene therapy 5: 1003–1007, 1998.*

Kozak, M. Point mutations define a sequence flanking the AUG initiator codon that modulates translation by eukaryotic ribosomes. Cell 44:283–292, 1986.*

Deonarain, M.P. Ligand–targeted receptor–mediated vectors for gene delivery. Exp. Opin. Ther. Patents 8:53–69, 1998.*

Verma, I.M. & Somia, N. Gene therapy–promises, problems and prosepect. Naure 389:239–242, 1997.*

Lewin, B. Genes VI. Oxford University Press, pp. 202–203, 1997.*

Dang et al.; Gene Therapy and Translational Cancer Research, 1999, Clinical Cancer Research vol. 5: 471–474.*

Ando et al., "Analyses of Mixed Melanogenesis in Tyrosinase cDNA—Transfected Human Amelanotic Melanoma Cells," J Invest Dermatol (1993) 101:864–870.

Beermann et al., "Molecular Characterization of the Mouse Tyrosinase Gene: Pigment Cell–Specific Expression in Transgenic Mice," Pigment Cell Research (1992) 5:295–299.

Bernan et al., "The Nucleotide Sequence of the Tyrosinase Gene from *Streptomyces Antibioticus* and Characterization of the Gene Product," Gene (1985) 37:101–110.

Della–Cioppa et al., "Melanin Production in *Escerichia Coli* from a Cloned Tyrosinase Gene," Biotechnology (1990) 8:634–638.

Geibal et al., "A Frequent Tyrosinase Gene Mutation in Classic, Tyrosinase—Negative (Type IA) Oculocutaneous Albinism," Proc Natl Acad SCI USA (1990) 87(9):3255–3258.

Kuster et al., Actinomycetes: The Boundary of Microorganisms, Ed. T. Arai, Tokyo: Toppan Co. (1976) 43–45.

Kwon et al., "Isolation and Sequence of a cDNA Clone for Human Tyrosinase that Maps at the Mouse c–Albino Locus," Proc Natl Acad SCI USA (1987) 84:7473–7477.

Lee et al., "A Trans–acting Gene is Required for the Phenotypic Expression of a Tyrosinase Gene in Streptomyces," Gene (1988) 65:71–81.

Muller et al., "Functional Analysis of Alternatively Spliced Tyrosinase Gene Transcripts," EMBO J (1988) 7:2723–2730.

Porter et al., "Multiple Alternatively Spliced Transcripts of the Mouse Tyrosinase–Encoding Gene," Gene (1991) 97:277–282.

Ruppert et al., "Multiple Transcripts of the Mouse Tyrosinase Gene are Generated by Alternative Splicing," EMBO J(1988) 7:2715–2722.

Tanaka et al., "Melanization in Albino Mice Transformed by Introducing Cloned Mouse Tyrosinase Gene," Development (1990) 108:223–227.

Tomita et al., "Human Oculocutaneous Albinism Caused by Single Base Insertion in the Tyrosinase Gene," Biochem Biophys Res Commun (1989) 164(3):990–996.

Yamamoto et al., "Melanin Production in Cultured Albino Melanocytes Transfected with Mouse Tyrosinase cDNA," Jpn J Genet (1989) 64:121–135.

Hoffman, "The Hair Follicles as a Gene Therapy Target," *Nature Biotechnology* (2000) 18:20–21.

Li et al., "The Feasibility of Targeted Selective Gene Therapy of the Hair Follicle,"*Nature Medicine* (1995) 1(7):705–706.

* cited by examiner

*Primary Examiner*—Dave T. Nguyen
*Assistant Examiner*—Quang Nguyen
(74) *Attorney, Agent, or Firm*—Morrison & Foerster LLP

(57) ABSTRACT

A composition and method for treating disorders related to tyrosinase gene expression and melanin biosynthesis is disclosed. The composition comprises a tyrosinase encoding nucleotide sequence and an ORF-438 encoding nucleotide sequence derived from Streptomyces, adapted for expression in mammalian cells. Also disclosed is a model system for evaluating agents that affect pigmentation.

11 Claims, 4 Drawing Sheets

```
                                                                    EcoRI
                                                      GAA TTC GCC GCC ACC ATG CCG
                                                                              Met Pro
GAA CTC ACC CGT CGT CGC GCG CTC GGC GCC GCA GCC GTC GTC GCC GCC GGT GTC CCG CTG
Glu Leu Thr Arg Arg Arg Ala Leu Gly Ala Ala Ala Val Val Ala Ala Gly Val Pro Leu
                                                                              SmaI
GTC GCC CTT CCC GCC GCC CGC GCG GAC GAT CGG GGG CAC CAC ACC CCC GAG GTC CCC GGG
Val Ala Leu Pro Ala Ala Arg Ala Asp Asp Arg Gly His His Thr Pro Glu Val Pro Gly
                                                  BglII
AAC CCG GCC GCG TCC GGC GCC CCC GCC GCC TTC GAC GAG ATC TAC AAG GGC CGC CGG ATA
Asn Pro Ala Ala Ser Gly Ala Pro Ala Ala Phe Asp Glu Ile Tyr Lys Gly Arg Arg Ile

CAG GGC CGG ACG GTC ACC GAC GGC GGG GGC CAC CAC GGC GGC GGT CAC GGC GGT GAC GGT
Gln Gly Arg Thr Val Thr Asp Gly Gly Gly His His Gly Gly Gly His Gly Gly Asp Gly

CAC GGC GGC GGC CAT CAC GGC GGC GGT TAC GCC GTG TTC GTG GAC GGC GTC GAA CTG CAT
His Gly Gly Gly His His Gly Gly Gly Tyr Ala Val Phe Val Asp Gly Val Glu Leu His

GTG ATG CGC AAC GCC GAC GGC TCG TGG ATC AGC GTC GTC AGC CAC TAC GAG CCG GTG GAC
Val Met Arg Asn Ala Asp Gly Ser Trp Ile Ser Val Val Ser His Tyr Glu Pro Val Asp
            SstII                       SaIGI   SstI
ACC CCG CGC GCC GCG GCC CGC GCT GCG GTC GAC GAG CTC CAG GGC GCC CGG CTC CTC CCC
Thr Pro Arg Ala Ala Ala Arg Ala Ala Val Asp Glu Leu Gln Gly Ala Arg Leu Leu Pro
                            BcLI
TTC CCC TCC AAC TAA GGA TCC      TTCGCCCCTCTCCCTCCCCCCCCCCTAACGTTACTGGCCGAAGCCGC
Phe Pro Ser Asn ***              AAGCGGGGAGAGGGAGGGGGGGGGGATTGCAATGACCGGCTTCGGCG

TTGGAATAAGGCCGGTGT   GCGTTTGTCTATATGTGATTTTCCACCATATTGCCGTCTTTTGGCAATGTGAGGGCCC
AACCTTATTCCGGCCACA   CGCAAACAGATATACACTAAAAGGTGGTATAACGGCAGAAAACCGTTACACTCCCGGG

GGAAACCTGGCC CTGTCTTCTTGACGAGCATTCCTAGGGGTCTTTCCCCTCTCGCCAAAGGAATGCAAGGTCTGTTG
CCTTTGGACCGG GACAGAAGAACTGCTCGTAAGGATCCCCAGAAAGGGGAGAGCGGTTTCCTTACGTTCCAGACAAC

AATGT CGTGAAGGAAGCAGTTCCTCTGGAAGCTTCTTGAAGACAAACAACGTCTGTAGCGACCCTTTGCAGGCAG
TTACA GCACTTCCTTCGTCAAGGAGACCTTCGAAGAACTTCTGTTTGTTGCAGACATCGCTGGGAAACGTCCGTC

CGGAACCCCCCACCTGGCGACAGCTGCCTCTGCGGCCAAAAGCCACGTGTATAAGATACACCTGCAAAGG CGGCAC
GCCTTGGGGGTGGACCGCTGTCCACGGAGACGCCGGTTTTCGGTGCACATATTCTATGTGGACGTTTCC GCCGTG

AACCCCAGTGCCACGTTGTGAGTTGGATAGTTGTGGAAAGAGTCAAATGGCTCTCCTCAAGCGT ATTCAACAAGGGG
TTGGGGTCACGGTGCAACACTCAACCTATCAACACCTTTCTCAGTTTACCGAGAGGAGTTCGCA TAAGTTGTTCCCC

CTGAAGGATGCCCAGAAGGTACCCCATTGTATGGGATCTGATCTGGGGCCTCGGTGCACATGCTTTACATGTGTTTAG
GACTTCCTACGGGTCTTCCATGGGGTAACATACCCTAGACTAGACCCCGGAGCCACGTGTACGAAATGTACACAAATC

TCGAGGTTAAAAAAGCTCTAGGCCCCCCGAACCACGGGGACGTGGTTTT CCTTTGAAAAACACGATGATAAT
AGCTCCAATTTTTTCGAGATCCGGGGGGCTTGGTGCCCCTGCACCAAAA GGAAACTTTTGTGCTACTATTA
```

FIG. 2A

```
                                                      XhoI
                                          CTC GAG GCC GCC ACC  ATG
                                                                Met
ACC GTC CGC AAG AAC CAG GCG TCC CTG ACC GCC GAG GAG AAG CGC CGC TTC GTC GCC GCC
Thr Val Arg Lys Asn Gln Ala Ser Leu Thr Ala Glu Gly Lys Arg Arg Phe Val Ala Ala

CTG CTC GAA CTC AAG CGC ACC GGC CGC TAC GAC GCC TTC GTC ACC ACG CAC AAC GCG TTC
Leu Leu Glu Leu Lys Arg Thr Gly Arg Tyr Asp Ala Phe Val Thr Thr His Asn Ala Phe

ATC CTG GGC GAC ACC GAC AAC GGC GAG CGC ACC GGC CAC CGT TCG CCG TCC TTC CTG CCC
Ile Leu Gly Asp Thr Asp Asn Gly Glu Arg Thr Gly His Arg Ser Pro Ser Phe Leu Pro

TGG CAC CGC AGA TTT CTG CTG GAG TTC GAG CGG GCG CTC CAG TCG GTG GAC GCG TCG GTG
Trp His Arg Arg Phe Leu Leu Glu Phe Glu Arg Ala Leu Gln Ser Val Asp Ala Ser Val

GCG CTG CCG TAC TGG GAC TGG TCC GCC GAC CGG TCC ACC CGG TCC TCG CTG TGG GCG CCG
Ala Leu Pro Tyr Trp Asp Trp Ser Ala Asp Arg Ser Thr Arg Ser Ser Leu Trp Ala Pro

GAC TTC CTC GGC GGC ACC GGG CGC AGC CGG GAC GGC CAG GTG ATG GAC GGG CCG TTC GCC
Asp Phe Leu Gly Gly Thr Gly Arg Ser Arg Asp Gly Gln Val Met Asp Gly Pro Phe Ala

GCG TCG GCC GGC AAC TGG CCG ATC AAT GTG CGG GTG GAC GGC CGT ACG TTC CTG CGG CGG
Ala Ser Ala Gly Asm Trp Pro Ile Asn Val Arg Val Asp Gly Arg Thr Phe Leu Arg Arg
                                                          SalGI
GCG CTC GGC GCG GGC GTG AGC GAA CTG CCC ACG CGT GCC GAG GTC GAC TCG GTG CTG GCG
Ala Leu Gly Ala Gly Val Ser Glu Leu Pre Thr Arg Ala Glu Val Asp Ser Val Leu Ala

ATG GCG ACG TAC GAC ATG GCG CCC TGG AAC AGC GGC TCC GAC GGC TTC CGC AAC CAT CTG
Met Ala Thr Tyr Asp Met Ala Pro Trp Asn Ser Gly Ser Asp Gly Phe Arg Asn His Leu

GAA GGG TGG CGC GGG GTC AAT CTG CAC AAC CGG GTG CAT GTC TGG GTC GGC GGC CAG ATG
Glu Gly Trp Arg Gly Val Asn Leu His Asn Arg Val His Val Trp Val Gly Gly Gln Met

GCG ACC GGG GTC TCC CCC AAC GAC CCG GTG TTC TGG CTG CAC CAC GCC TAC ATC GAC AAG
Ala Thr Gly Val Ser Pro Asn Asp Pro Val Phe Trp Leu His His Ala Tyr Ile Asp Lys

CTG TGG GCC GAG TGG CAG CGG CGG CAC CCC TCG TCC CCG TAT CTG CCG GGC GGC GGC ACG
Leu Trp Ala Glu Trp Gln Arg Arg His Pro Ser Ser Pro Tyr Leu Pro Gly Gly Gly Thr
         SalGI
CCG AAC GTC GTC GAC CTC AAC GAG ACG ATG AAG CCG TGG AAC GAC ACC ACC CCG GCG GCC
Pro Asn Val Val Asp Leu Asn Glu Thr Met Lys Pro Trp Asn Asp Thr Thr Pro Ala Ala
                                                      BamHI
CTG CTG GAC CAC ACC CGG CAC TAC ACC TTC GAC GTC TAA GGA TCC
Leu Leu Asp His Thr Arg His Tyr Thr Phe Asp Val ***
```

FIG. 2B

SEQUENCE LISTING

```
<160> NUMBER OF SEQ ID NOS: 12

<210> SEQ ID NO 1
<211> LENGTH: 9
<212> TYPE: DNA
<213> ORGANISM: Artificial Sequence
<220> FEATURE:
<223> OTHER INFORMATION: Kozak consensus sequence

<400> SEQUENCE: 1 gccgccacc                                                              9

<210> SEQ ID NO 2
<211> LENGTH: 36
<212> TYPE: DNA
<213> ORGANISM: Artificial sequence
<220> FEATURE:
<223> OTHER INFORMATION: ORF-438 upstream primer

<400> SEQUENCE: 2
cggaattcgc cgccaccatg ccggaactca cccgtc                                36

<210> SEQ ID NO 3
<211> LENGTH: 34
<212> TYPE: DNA
<213> ORGANISM: Artificial Sequence
<220> FEATURE:
<223> OTHER INFORMATION: ORF-438 downstream primer

<400> SEQUENCE: 3
ggctgatcat tagttggagg ggaaggggag gagc                                  34

<210> SEQ ID NO 4
<211> LENGTH: 34
```

```
<212> TYPE: DNA
<213> ORGANISM: Artificial Sequence
<220> FEATURE:
<223> OTHER INFORMATION: Tyrosinase upstream primer

<400> SEQUENCE: 4
ctcgaggccg ccgccatgac cgtccgcaag aacc                              34

<210> SEQ ID NO 5
<211> LENGTH: 28
<212> TYPE: DNA
<213> ORGANISM: Artificial Sequence
<220> FEATURE:
<223> OTHER INFORMATION: Tyrosinase downstream primer

<400> SEQUENCE: 5
ggatccttag acgtcgaagg tgtagtgc                                     28

<210> SEQ ID NO 6
<211> LENGTH: 28
<212> TYPE: DNA
<213> ORGANISM: Artificial Sequence
<220> FEATURE:
<223> OTHER INFORMATION: Upstream primer

<400> SEQUENCE: 6
ggctgatcat tcgcccctct ccctcccc                                     28

<210> SEQ ID NO 7
<211> LENGTH: 30
<212> TYPE: DNA
<213> ORGANISM: Artificial Sequence
<220> FEATURE:
<223> OTHER INFORMATION: Downstream primer

<400> SEQUENCE: 7
agcggccatt atcatcgtgt ttttcaaagg                                   30

<210> SEQ ID NO 8
<211> LENGTH: 459
<212> TYPE: DNA
<213> ORGANISM: Artificial Sequence
<220> FEATURE:
<221> NAME/KEY: CDS
<222> LOCATION: (16)...(450)
<223> OTHER INFORMATION: ORF 438 gene

<400> SEQUENCE: 8
gaattcgccg ccacc atg ccg gaa ctc acc cgt cgt cgc gcg ctc ggc gcc    51
                 Met Pro Glu Leu Thr Arg Arg Arg Ala Leu Gly Ala
                  1               5                  10 gca gcc gtc gtc gcc gcc ggt gtc ccg ctg stc gcc ctt ccc gcc gcc    99
Ala Ala Val Val Ala Ala Gly Val Pro Leu Xaa Ala Leu Pro Ala Ala
         15                  20                  25 cgc gcg gac gat cgg ggg cac acc ccc gag gtc ccc ggg aac ccg gcc   147
Arg Ala Asp Asp Arg Gly His Thr Pro Glu Val Pro Gly Asn Pro Ala
         30                  35                  40 gcg tcc ggc gcc ccc gcc gcc ttc gac gag atc tac aag ggc cgc cgg   195
Ala Ser Gly Ala Pro Ala Ala Phe Asp Glu Ile Tyr Lys Gly Arg Arg
 45                  50                  55                  60 ata cag ggc cgg acg gtc acc gac ggc ggg ggc cac cac ggc ggc ggt   243
Ile Gln Gly Arg Thr Val Thr Asp Gly Gly Gly His His Gly Gly Gly
                 65                  70                  75 cac ggc ggt gac ggt cac ggc ggc ggc cat cac ggc ggc ggt tac gcc   291
His Gly Gly Asp Gly His Gly Gly Gly His His Gly Gly Gly Tyr Ala
```

```
gtg ttc gtg gac ggc gtc gaa ctg cat gtg atg cgc aac gcc gac ggc       339
Val Phe Val Asp Gly Val Glu Leu His Val Met Arg Asn Ala Asp Gly
         95                 100                 105 tcg tgg atc agc gtc gtc agc cac tac gag ccg gtc gac acc ccg cgc       387
Ser Trp Ile Ser Val Val Ser His Tyr Glu Pro Val Asp Thr Pro Arg
        110                 115                 120 gcc gcg gcc cgc gct gcg gtc gac gag ctc cag ggc gcc cgg ctc ctc       435
Ala Ala Ala Arg Ala Ala Val Asp Glu Leu Gln Gly Ala Arg Leu Leu
125                 130                 135                 140 ccc ttc ccc tcc aac taaggatcc                                         459
Pro Phe Pro Ser Asn
                145
```

<210> SEQ ID NO 9
<211> LENGTH: 145
<212> TYPE: PRT
<213> ORGANISM: Artificial Sequence
<220> FEATURE:
<223> OTHER INFORMATION: Deduced amino acid sequence of SEQ ID NO:8
<221> NAME/KEY: VARIANT
<222> LOCATION: (1)...(145)
<223> OTHER INFORMATION: Xaa = Any Amino Acid

<400> SEQUENCE: 9

```
Met Pro Glu Leu Thr Arg Arg Arg Ala Leu Gly Ala Ala Ala Val Val
1               5                   10                  15

Ala Ala Gly Val Pro Leu Xaa Ala Leu Pro Ala Ala Arg Ala Asp Asp
            20                  25                  30

Arg Gly His Thr Pro Glu Val Pro Gly Asn Pro Ala Ala Ser Gly Ala
        35                  40                  45

Pro Ala Ala Phe Asp Glu Ile Tyr Lys Gly Arg Arg Ile Gln Gly Arg
    50                  55                  60

Thr Val Thr Asp Gly Gly His His Gly Gly His Gly Gly Asp
65                  70                  75                  80

Gly His Gly Gly Gly His His Gly Gly Gly Tyr Ala Val Phe Val Asp
            85                  90                  95

Gly Val Glu Leu His Val Met Arg Asn Ala Asp Gly Ser Trp Ile Ser
        100                 105                 110

Val Val Ser His Tyr Glu Pro Val Asp Thr Pro Arg Ala Ala Ala Arg
    115                 120                 125

Ala Ala Val Asp Glu Leu Gln Gly Ala Arg Leu Leu Pro Phe Pro Ser
    130                 135                 140

Asn
145
```

<210> SEQ ID NO 10
<211> LENGTH: 580
<212> TYPE: DNA
<213> ORGANISM: Artificial Sequence
<220> FEATURE:
<223> OTHER INFORMATION: IRES gene

<400> SEQUENCE: 10

```
ttcgccctc tccctcccc cccctaacg ttactggccg aagccgcttg gaataaggcc        60
ggtgtgcgtt tgtctatatg tgattttcca ccatattgcc gtcttttggc aatgtgaggg    120
cccggaaacc tggccctgtc ttcttgacga gcattcctag gggttctttc ccctctcgcc    180
aaaggaatgc aaggtctgtt gaatgtcgtg aaggaagcag ttcctctgga agcttcttga    240
```

-continued

```
agacaaacaa cgtctgtagc gacccttttgc aggcagcgga acccccacc tggccgacag        300 gtgcctctgc ggccaaaagc cacgtgtata agatacacct gcaaaggcgg cacaacccca        360
gtgccacgtt gtgagttgga tagttgtgga aagagtcaaa tggctctcct caagcgtatt        420
caacaagggg ctgaaggatg cccagaaggt accccattgt atgggatctg atctggggcc        480
tcggtgcaca tgctttacat gtgtttagtc gaggttaaaa aagctctagg cccccgaac        540 cacggggacg tggttttcct ttgaaaaaca cgatgataat                              580

<210> SEQ ID NO 11
<211> LENGTH: 843
<212> TYPE: DNA
<213> ORGANISM: Artificial Sequence
<220> FEATURE:
<221> NAME/KEY: CDS
<222> LOCATION: (16)...(834)
<223> OTHER INFORMATION: Tyrosinase gene

<400> SEQUENCE: 11
ctcgaggccg ccacc atg acc gtc cgc aag aac cag gcg tcc ctg acc gcc        51
                 Met Thr Val Arg Lys Asn Gln Ala Ser Leu Thr Ala
                  1               5                  10 gag gag aag cgc cgc ttc gtc gcc gcc ctg ctc gaa ctc aag cgc acc        99
Glu Glu Lys Arg Arg Phe Val Ala Ala Leu Leu Glu Leu Lys Arg Thr
             15                  20                  25 ggc cgc tac gac gcc ttc gtc acc acg cac aac gcg ttc atc ctg ggc       147
Gly Arg Tyr Asp Ala Phe Val Thr Thr His Asn Ala Phe Ile Leu Gly
         30                  35                  40 gac acc gac aac ggc gag cgc acc ggc cac cgt tcg ccg tcc ttc ctg       195
Asp Thr Asp Asn Gly Glu Arg Thr Gly His Arg Ser Pro Ser Phe Leu
 45                  50                  55                  60 ccc tgg cac cgc aga ttt ctg ctg gag ttc gag cgg gcg ctc cag tcg       243
Pro Trp His Arg Arg Phe Leu Leu Glu Phe Glu Arg Ala Leu Gln Ser
                 65                  70                  75 gtg gac gcg tcg gtg gcg ctg ccg tac tgg gac tgg tcc gcc gac cgg       291
Val Asp Ala Ser Val Ala Leu Pro Tyr Trp Asp Trp Ser Ala Asp Arg
             80                  85                  90 tcc acc cgg tcc tcg ctg tgg gcg ccg gac ttc ctc ggc ggc acc ggg       339
Ser Thr Arg Ser Ser Leu Trp Ala Pro Asp Phe Leu Gly Gly Thr Gly
         95                 100                 105 cgc agc cgg gac ggc cag gtg atg gac ggg ccg ttc gcc gcg tcg gcc       387
Arg Ser Arg Asp Gly Gln Val Met Asp Gly Pro Phe Ala Ala Ser Ala
    110                 115                 120 ggc aac tgg ccg atc aat gtg cgg gtg gac ggc cgt acg ttc ctg cgg       435
Gly Asn Trp Pro Ile Asn Val Arg Val Asp Gly Arg Thr Phe Leu Arg
125                 130                 135                 140 cgg gcg ctc ggc gcg ggc gtg agc gaa ctg ccc acg cgt gcc gag gtc       483
Arg Ala Leu Gly Ala Gly Val Ser Glu Leu Pro Thr Arg Ala Glu Val
                145                 150                 155 gac tcg gtg ctg gcg atg gcg acg tac gac atg gcg ccc tgg aac agc       531
Asp Ser Val Leu Ala Met Ala Thr Tyr Asp Met Ala Pro Trp Asn Ser
            160                 165                 170 ggc tcc gac ggc ttc cgc aac cat ctc gaa ggg tgg cgc ggg gtc aat       579
Gly Ser Asp Gly Phe Arg Asn His Leu Glu Gly Trp Arg Gly Val Asn
        175                 180                 185
```

-continued

```
ctg cac aac cgg ctg cat gtc tgg gtc ggc ggc cag atg gcg acc ggg    627
Leu His Asn Arg Leu His Val Trp Val Gly Gly Gln Met Ala Thr Gly
        190                 195                 200 gtc tcc ccc aac gac ccg gtg ttc tgg ctg cac cac gcc tac atc gac    675
Val Ser Pro Asn Asp Pro Val Phe Trp Leu His His Ala Tyr Ile Asp
205                 210                 215                 220 aag ctg tgg gcc gag tgg cag cgg cgg cac ccc tcg tcc ccg tat ctg    723
Lys Leu Trp Ala Glu Trp Gln Arg Arg His Pro Ser Ser Pro Tyr Leu
                    225                 230                 235 ccg ggc ggc ggc acg ccg aac gtc gtc gac ctc aac gag acg atg aag    771
Pro Gly Gly Gly Thr Pro Asn Val Val Asp Leu Asn Glu Thr Met Lys
                240                 245                 250 ccg tgg aac gac acc acc ccg gcg gcc ctg ctg gac cac acc cgg cac    819
Pro Trp Asn Asp Thr Thr Pro Ala Ala Leu Leu Asp His Thr Arg His
            255                 260                 265 tac acc ttc gac gtc taaggatcc                                      843
Tyr Thr Phe Asp Val
    270
```

<210> SEQ ID NO 12
<211> LENGTH: 273
<212> TYPE: PRT
<213> ORGANISM: Artificial Sequence
<220> FEATURE:
<223> OTHER INFORMATION: Deduced amino acid sequence of SEQ ID NO:11

<400> SEQUENCE: 12

```
Met Thr Val Arg Lys Asn Gln Ala Ser Leu Thr Ala Glu Glu Lys Arg
1               5                   10                  15

Arg Phe Val Ala Ala Leu Leu Glu Leu Lys Arg Thr Gly Arg Tyr Asp
            20                  25                  30

Ala Phe Val Thr Thr His Asn Ala Phe Ile Leu Gly Asp Thr Asp Asn
        35                  40                  45

Gly Glu Arg Thr Gly His Arg Ser Pro Ser Phe Leu Pro Trp His Arg
    50                  55                  60

Arg Phe Leu Leu Glu Phe Glu Arg Ala Leu Gln Ser Val Asp Ala Ser
65                  70                  75                  80

Val Ala Leu Pro Tyr Trp Asp Trp Ser Ala Asp Arg Ser Thr Arg Ser
                85                  90                  95

Ser Leu Trp Ala Pro Asp Phe Leu Gly Gly Thr Gly Arg Ser Arg Asp
            100                 105                 110

Gly Gln Val Met Asp Gly Pro Phe Ala Ala Ser Ala Gly Asn Trp Pro
        115                 120                 125

Ile Asn Val Arg Val Asp Gly Arg Thr Phe Leu Arg Arg Ala Leu Gly
    130                 135                 140

Ala Gly Val Ser Glu Leu Pro Thr Arg Ala Glu Val Asp Ser Val Leu
145                 150                 155                 160

Ala Met Ala Thr Tyr Asp Met Ala Pro Trp Asn Ser Gly Ser Asp Gly
                165                 170                 175

Phe Arg Asn His Leu Glu Gly Trp Arg Gly Val Asn Leu His Asn Arg
            180                 185                 190

Leu His Val Trp Val Gly Gly Gln Met Ala Thr Gly Val Ser Pro Asn
        195                 200                 205

Asp Pro Val Phe Trp Leu His His Ala Tyr Ile Asp Lys Leu Trp Ala
    210                 215                 220

Glu Trp Gln Arg Arg His Pro Ser Ser Pro Tyr Leu Pro Gly Gly Gly
225                 230                 235                 240
```

-continued

```
Thr Pro Asn Val Val Asp Leu Asn Glu Thr Met Lys Pro Trp Asn Asp
            245                 250                 255

Thr Thr Pro Ala Ala Leu Leu Asp His Thr Arg His Tyr Thr Phe Asp
            260                 265                 270

Val
```

METHOD AND MODEL FOR HAIR PIGMENTATION

This application claims priority under 35 USC 119 from provisional application No. 60/105,725 filed Oct. 27, 1998 the contents of which are incorporated herein by reference.

TECHNICAL FIELD

The invention generally relates to compositions and methods for treating disorders related to tyrosinase gene expression and melanin biosynthesis. In addition, the invention relates to a model for pigmentation of hair.

BACKGROUND ART

Treatment of the hair and skin with various creams or lotions with biologically active ingredients to improve hair growth and pigmentation has generally been unsatisfactory. A wide variety of externally applied agents available are said to improve body, flexibility, curl and hair color. These have limited and only short term usefulness. In particular, coloring hair with various dyes requires frequent repetitions and is not always natural in appearance. The invention provides improved alternatives, focused on tyrosinase.

Tyrosinase is a ubiquitously distributed copper-containing monoxygenase that is essential for melanin biosynthesis in pigment cells. It catalyzes the conversion of tyrosine to dihydroxyphenylalanine (DOPA) and the conversion of DOPA to dopaquinone, referred to as tyrosine hydroxylase activity and DOPA oxidase activity, respectively.

Disorders of tyrosinase gene expression and melanin biosynthesis are related to many diseases involving pigmentation such as albinism, hair pigment loss, and vitellego. Tyrosinase is a key enzyme for melanin synthesis in vertebrate pigment cells, melanocytes, and retinal pigment epithelial cells. Tyrosinase is absent in human white hair bulbs, as well as in albino epithelial cells. Thus, the loss of tyrosinase could be the basis of pigment loss in hair. It is also believed that tyrosinase activity is abnormal in Parkinson's disease. Tyrosinase is expressed in brain cells in the substantia nigra, forebrain, and midbrain, thus tyrosinase could be implicated in neuromelanin formation in the substantia nigra and thus related to neurodegenerative disorders.

The murine and human tyrosinase genes have been cloned. (Kwon et al. *Proc Natl Acad Sci USA* (1987) 84:7473–7477; Yamamoto et al. *Jpn J Genet* (1989) 64:121–135; Ruppert et al. *EMBO J* (1988) 7:2715–2722. The structural genes for human and murine tyrosinase have long DNA sequences. In mice, the structural gene for tyrosinase is located on the c-locus of chromosome 7, which spans a region of more than 70 kb. In humans, the tyrosinase gene is located on the c-locus on chromosome 11. It has been reported that only the full complement of five exons were able to confer tyrosinase enzyme activity to tyrosinase-negative cells.

Murine and human tyrosinase cDNAs have been expressed in mammalian cells after transfection. See Muller et al. (1988), Tomita et al. (1989), Yamamoto et al. (1989) supra, Geibal et al. (1990), Porter et al. *Gene* (1991) 97:277–282; Mishima et al. (1993), and U.S. Pat. No. 5,753,263. Several cDNA clones of the mouse tyrosinase have been isolated independently. Among those cDNA clones, there are several differences in the deduced amino acid sequence. Muller et al. (1988) supra reported that one of their cDNA clones, pmcTYr1, possessed the coding capacity for tyrosinase, and they demonstrated that pmc-TYr1 could be inserted in cultured human amelanotic melanoma cells. However, they did not report any pigment production. On the other hand, Yamamoto et al. (1989) supra constructed the mouse tyrosinase cDNA minigene, mg-Tyr1-J which was ligated with a genomic 5'-non-coding flanking sequence and transfected cultured albino melanocytes, which produced tyrosinase and melanin.

The tyrosinase gene in albino mice has a single base-pair mutation in exon 1 which results in a nonfunctional tyrosinase protein and absence of melanin in the albino melanocytes. Melanin has been produced in amelanotic melanocytes in transgenic albino mice whose fertilized eggs were inserted with a normal mouse tyrosinase transgene, and melanin was seen in the hair bulbs, hair shafts, choroid, and pigment epithelium. Tanaka et al. *Development* (1990) 108:223–227; Beerman et al. *Pigment Cell Research* (1992) 5:295–299. Human tyrosinase cDNA has been used to transfect amelanotic melanoma cells and induce melanin production. Ando et al. *J Invest Dermatol* (1993) 101:864–870.

The human and murine tyrosinase constructs are difficult to manipulate due to their complexity and size. Many species of Streptomyces are also capable of forming melanin due to the expression of tyrosinase from the mel operon. See Kuster et al. (1976) Chromogenicity of actinomycetes. Actinomycetes: The Boundary of Microorganisms. Ed. T. Arai, Tokyo: Toppan Co. 43-45. The 1.2 kb mel locus of *S. antibioticus* has been cloned and sequenced and shown to contain a structural tyrosinase gene and an open reading frame ORF-438. The ORF-438 protein regulates copper incorporation, which is essential for the expression and function of tyrosinase and melanin production in Streptomyces. The ORF-438 and tyrosinase genes are transcribed from the same promoter located in the 5'-region adjacent to ORF438, thereby indicating that these genes form an operon. Beman et al. *Gene* (1985) 37:101–110. The ORF-438 protein functions as a transactivator of tyrosinase. See Lee et al. *Gene* (1988) 65:71–81. The ORF-438 protein also delivers copper to apotyrosinase to generate active tyrosinase. Production of melanin in *E. coli* from the mel locus of *S. antibioticus* was dependent on the coexpression of a full length ORF-438 gene as well as the tyrosinase gene. See Della-Cioppa et al. *Biotechnology* (1990) 8:634–638.

Advantage has been taken of the characteristics of the mel operon which is smaller in size, lacks introns, and exhibits a potential for high expression to construct vectors useful to construct models for pigmentation disorders and for treatment of tyrosinase deficiency.

SUMMARY OF THE INVENTION

Generally, the present invention is directed to compositions and methods for treating disorders related to tyrosinase gene expression and melanin biosynthesis, and to model systems for such disorders.

In one aspect, the invention is directed to a nucleic acid molecule comprising a bicistronic nucleotide sequence for efficient production of a functional Streptomyces tyrosinase in mammalian cells comprising a tyrosinase encoding nucleotide sequence and nucleotide sequence encoding ORF-438, coupled through an internal ribosome entry sequence (IRES).

In another aspect, the invention is directed to a method for treating a tyrosinase deficiency or pigmentation disorder in a subject which method comprises modifying the cells of the subject with the expression system of the invention. In a preferred embodiment, the cells to be treated are hair follicle cells and the subjects are mammals, such as primates, including humans, domestic animals, and rodents. The expression system can be utilized as the sole method of treatment, but the system may be used in combination with administration of other beneficial compounds such as proteins, pigments, dyes, growth regulators and other compounds which affect the characteristics of skin and hair. Thus, the expression system may be utilized in addition to cell cycle regulating proteins or the multi-drug resistance proteins which confer resistance to chemotherapy-induced alopecia.

In another aspect, the invention is directed to cells modified to contain the expression system of the invention for the expression of active tyrosinase and production of melanin. In another aspect, the invention is directed to a nonhuman animal comprising the modified cells. The invention is also directed to vectors which comprise the nucleotide sequence encoding tyrosinase and a protein for the incorporation of copper.

In another embodiment, the invention is directed to a method to monitor the effect of compounds or protocols on pigment disorders using histocultures of cells containing the expression systems of the invention.

BRIEF DESCRIPTION OF THE DRAWINGS

FIGS. 2A and 2B show the nucleotide sequence of the bicistronic pLmelSN insert (SEQ ID NOs: 8–12); as indicated, both the ORF-438 and tyrosinase sequences are preceded by the Kozak sequence and terminated with TAA.

DETAILED DESCRIPTION OF THE INVENTION

Figure 1:
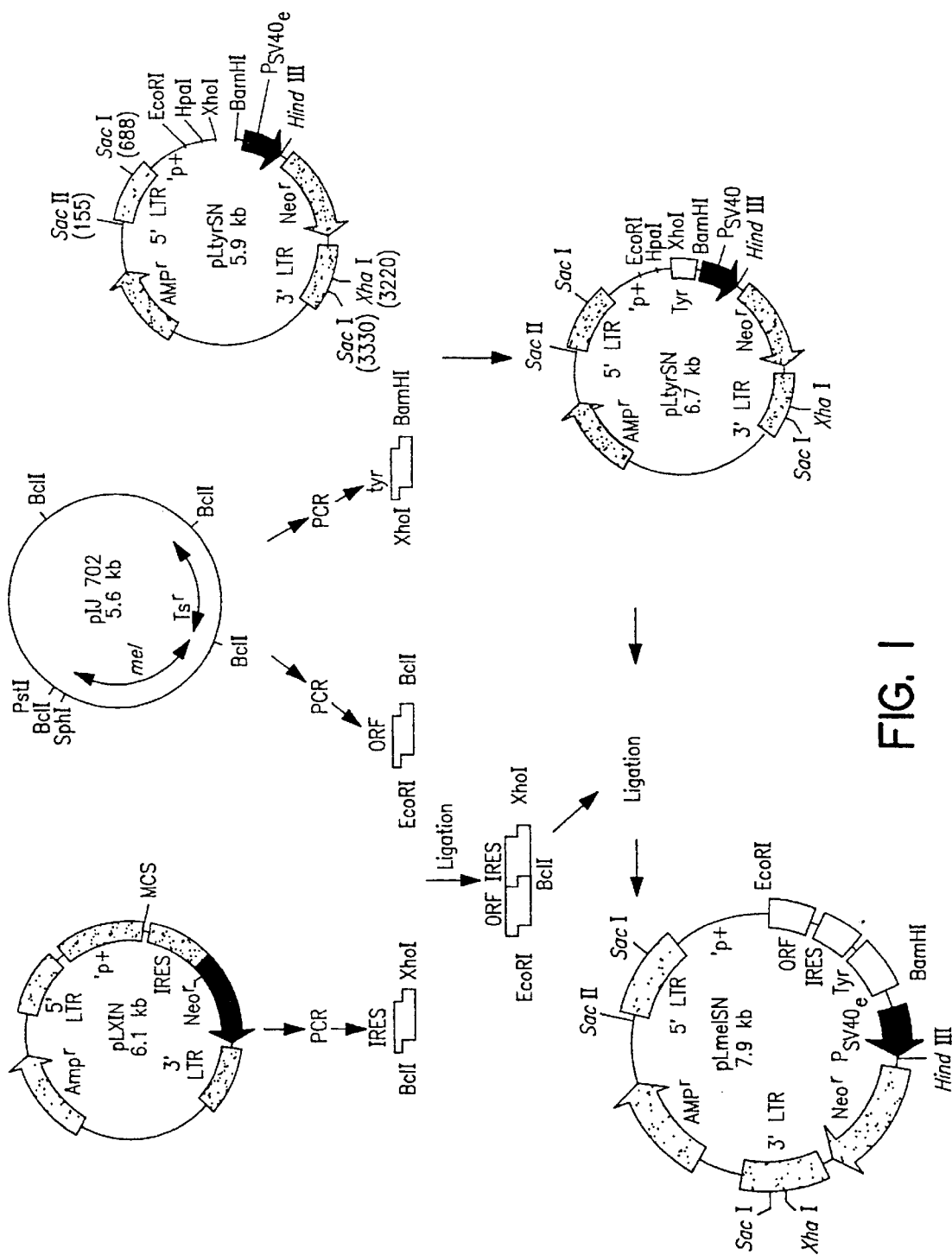
FIG. 1 shows schematically shows how the retroviral vector pLmelSN was constructed.

Tyrosinase is the key enzyme for melanin biosynthesis. Disorders of tyrosinase activity include Parkinson's disease, vitellego and albinism. As described herein, this invention provides a method of genetically modifying tyrosinase expression and melanin production.

Thus, the invention provides uniquely effective protocols and materials for the treatment of disorders related to tyrosinase activity, as well as assay systems for monitoring the production of tyrosinase or melanin in cells. In particular, the invention provides protocols and materials for treating pigmentation disorders, as well as assay systems for monitoring the effect of various treatments on production of tyrosinase or melanin in hair follicle cells.

The expression systems employed in the present invention generally comprise a bicistronic nucleotide sequence comprising a modified *Streptomyces* mel locus. The bicistronic nucleotide sequence which comprises a tyrosinase encoding portion, an ORF438 encoding portion and an IRES coupling the two components, can be arranged in either order. That is, as shown in FIG. 2, the construct may contain the sequence encoding ORF438 followed by the IRES followed by the gene encoding tyrosinase or, conversely, the tyrosinase encoding portion may be followed by IRES followed by ORF438. Typically, the bicistronic nucleotide sequence is inserted into a vector which contains control sequences operably linked to the bicistronic sequence for delivery to the intended cell, typically hair follicles. However, as is understood in the art, the bicistronic sequence of the invention may be inserted into a host cell so as to effect expression under control of endogenous promoters and terminating sequences. Vectors for delivery of the nucleotide sequence may be designed to replicate extrachromosomally but preferably may effect the insertion of the nucleotide sequence into the genome of the host, and thus may employ endogenous control sequences to effect expression. The nucleotide sequence to be inserted may be coupled to sequences which effect homologous recombination at known targets in the genome; random integration into the genome may be relied upon, or a retroviral vector may be employed. Use of viral vectors especially retroviral vectors containing the expression system of the invention is a preferred method.

Retroviral vectors have been widely used in gene therapy studies. See Jolly et al. (1997) Viral Vector Systems for Gene Therapy. The Internet Book of Gene Therapy.

Eds. Sobol, R. E. and Scanlon, K. J. Stamford, Conn., Appleton and Lange, pp. 3–16. Retroviral vectors integrate a DNA copy of their genome into the host chromosome, thereby allowing for stable transmission of vector sequences to descendent cells, making long-term expression of transgenes possible. While retroviral vectors are preferred, other viral based methods may also be employed, such as Herpes simplex vectors, Wolfe, J. H., et al. *Nature Genetics* (1992) 1:379–384, or adenovirus vectors such as Ad2 or Ad5. These viruses are not oncogenic and are relatively stable and easy to manipulate. The complete genomes of Ad2 and Ad5 are known and there are a number of known mutants that have been made available for genetic therapy in general. Berkner, K. L., *Biotechniques* (1988) 6:612–629. However, while viral-based vectors are preferred, any suitable vector for transformation can be employed.

If viral vectors are used, the specificity of infectivity can be enhanced by including receptor-binding moieties in the vector. It is known in the art to modify viral surface molecules with binding domains of ligands, such as erythropoietin which targets erythroleukemia, heregulin which targets breast cancer and neurotensin which targets the colon. Thus, viral surface molecules may be modified to contain binding domains of ligands which target hair follicle cells or other cells related to hair and skin pigmentation.

The expression system of the invention employs suitable promoters and enhancers. General constitutive promoters such as SV40 or CMV promoters can be included, along with their enhancer elements, or tissue-specific promoters may be used to enhance specificity. Means to construct suitable vectors for delivery of a gene along with provision for its expression are well known in the art.

In order to effect the modification of cells for the expression of tyrosinase and the production of melanin, the expression system or integrating encoding nucleotide sequence must be formulated so as to enter the cell. Integration of the desired nucleotide sequences into viral vectors provides this means of entry. However, other mediators of cellular uptake, such as lipids, or various liposomal type compositions or emulsions may also be employed.

The composition, comprising a nucleotide sequence encoding a protein with tyrosinase activity, preferably operably linked control sequences, or sequences effecting genomic integration, thus may contain a means for effecting cellular uptake. This composition is supplied to the cells, either in vitro or in vivo. In vitro administration is particularly helpful in assessing, in advance, the efficacy of the therapeutic approach for a particular individual, as well as expression and production levels of the tyrosinase and melanin in the cells.

Additionally, the expression system may be delivered into the skin without a carrier. For example, naked DNA may be introduced into the skin by direct injection, by gene gun, or by using an electric pulse. See Furth et al. Hybridoma (1996) 14:149–152; Hengge et al. *Nature Genet* (1995) 110:161–166; Ciernik et al. *Hum Gene Ther* (1996) 7:893–899; Williams et al. *Proc Natl Acad Sci USA* (1991) 88:2726–2730; Zhang et al. *Biochem Biophys Res Commun* (1996) 220:633–636. Topical application of the expression system as naked plasmid DNA comprising a tyrosinase gene and a gene which encodes a protein that regulates copper incorporation such as ORF-438 from *S. antibioticus* is also contemplated as a gene therapy method for treating disorders related to tyrosinase expression and melanin production. The expression system may be applied directly to the skin by the various methods known in the art. See Fan et al. *Nature Biotech* (1990) 17:870–872; Yu et al. *J Invest Dermatology* (1999) 112:370–375; Tang et al. *Nature* (1997) 338:729–730. The expression system may also be delivered by genetic vaccination or polynucleotide vaccination as described by Shi et al. *Vaccine* (1999) 17(17):2136–41, Falo, L. D. *Proc Assoc Am Physicians* (1999) 111(3):211–9, and Tuting et al. *J Invest Dermatol* (1998) 111(2):183–8.

It may be advantageous in some contexts to employ the protein having tyrosinase activity as a fusion protein to a reporter amino acid sequence, most preferably an amino acid sequence which confers fluorescence on the fusion protein. The use of green fluorescent protein (GFP) to confer fluorescence on a fusion protein is well understood in the art; see, for example, Chalfie, M., et al. *Science* (1994) 263:802–805. The expression system may be targeted to the cells of interest, such as hair follicle cells by utilizing liposome-mediated delivery as described in U.S. Pat. No. 5,641,508, incorporated herein by reference.

The invention contemplates using the bicistronic nucleotide sequence to study and treat diseases associated with tyrosinase expression such as Parkinson's disease, albinism, hair pigment loss and vitellego. Similarly, the invention contemplates using the expression system in in vitro and animal models to determine the effects of various substances on pigmentation. In both cases, cells which exhibit tyrosinase abnormalities, whether contained in vitro or in vivo, must be accessed by the bicistronic nucleotide sequence in such a fashion as to exact its expression. For use in evaluating protocols or compounds for their effect on pigmentation, generally the cells are modified in vitro or in vivo and maintained in a histoculture. Cell cultures can be modified in vitro with a variety of methods including electroporation, lipofection, viral infection, osmotic alteration, and the like. They can then be cultured in a three-dimensional matrix as is understood in the art. Alternatively, for either treatment or formation of histocultures, cells can be modified in vivo by administering the subject harboring such cells a suitable composition containing the required sequences. Such administration may include the use of "naked DNA," viral vectors which infect, for example, the skin or hair follicles when applied topically, or by other methods known in the art. Sections of the skin, preferably containing hair follicles, can then be made the basis for histoculture.

The invention also includes treating the cells, with a wide variety of beneficial or otherwise therapeutic compounds in addition to the tyrosinase expression system through viral vector-mediated systems as described herein. The therapeutic compounds can be nucleic acids, hormones, proteins, enzymes, vitamins and other biochemical co-factors deemed to provide a therapeutic effect upon a hair or skin cell's growth, condition, color and the like. Particularly preferred are agents which improve the growth of the hair shaft, agents which stimulate the production of hair coloring pigments in the hair follicle, agents which replace pigment in the follicle cell or hair shaft (i.e., restore hair color), agents which stimulate hair growth, and agents which prevent hair loss. Most preferred are cell cycle inhibitors which prevent alopecia. Other agents useful in conditions of hair loss (alopecia) are those which stimulate hair growth, or those which inhibit the hair loss. Hair growth stimulators are generally well known, and include minoxidil, cyclosporin and the like known hair growth stimulators.

The invention additionally contemplates the administration of any gene beneficial to hair follicles through viral vector-mediated systems as described herein. A gene is beneficial to hair follicles where it confers, upon selective delivery to the hair follicles by the present methods, a beneficial effect upon the hair follicle. Exemplary beneficial genes include genes normally and preferentially expressed in hair follicle, and therefore important for normal gene function. Beneficial genes can be identified by any of a variety of molecular biological methods. For example, a cDNA library of expressed genes can be prepared from hair follicle tissue supporting healthy hair, and can be enriched by subtractive hybridization against a cDNA library derived from a non-hair-producing or vellus-hair-producing follicle tissue, thereby producing a library of cDNA molecules whose expression is specific to hair follicles. Individual cDNA molecules from the hair specific cDNA library can be further screened for therapeutic effectiveness using the skin histoculture assay described in U.S. Pat. No. 5,641,508.

In one preferred embodiment, the invention contemplates a method for restoring hair color in mammals, particularly human, in which the hair color is graying for any of a variety of reasons, including age. The method comprises applying a therapeutically effective amount of the bicistronic sequence of the invention to a skin area on the mammal having a plurality of hair follicles which exhibit fading or graying hair color. A therapeutically effective amount is the amount of a nucleic acid needed for the expression of tyrosinase and the production of melanin in the cells of the hair follicles. The application of the relevant expression system or bicistronic sequence per se can be repeated at defined intervals to provide prolonged effectiveness, as needed.

As used herein, the terms such as "pharmaceutically acceptable" and the like as related to compositions, carriers, diluents and reagents, represent that the materials are capable of administration upon a mammal or human without the production of undesirable physiological effects such as nausea, dizziness, gastric upset and the like.

The preparation of a pharmacological composition that contains active ingredients dispersed therein is well understood in the art. Typically such compositions are prepared as sterile compositions either as liquid solutions or suspensions, aqueous or non-aqueous, however, suspensions in liquid prior to use can also be prepared.

The active ingredient can be mixed with excipients which are pharmaceutically acceptable and compatible with the active ingredient and in amounts suitable for use in the therapeutic methods described herein. Suitable excipients are, for example, water, saline, dextrose, glycerol, ethanol or the like and combinations thereof In addition, if desired, the composition can contain minor amounts of auxiliary substances such as wetting or emulsifying agents, pH buffering agents and the like which enhance the effectiveness of the active ingredient.

Liquid compositions can also contain liquid phases in addition to and to the exclusion of water. Exemplary of such additional liquid phases are glycerin, vegetable oils such as cottonseed oil, organic esters such as ethyl oleate, and water-oil emulsions.

A therapeutic composition contains the expression system of the present invention. A therapeutically effective amount of the expression system and, if present, other beneficial compounds, is a predetermined amount calculated to achieve the desired effects, i.e., to effectively affect the pigmentation of the skin or hair cells. Thus, an effective amount can be measured by improvements in one or more symptoms associated skin or hair cell pigmentation in the subject.

The dosage can be adjusted by the individual physician in the event of any complication. The compositions are administered in a manner compatible with the dosage formulation, and in a therapeutically effective amount. The quantity to be administered depends on the subject to be treated, capacity of the subject's system to utilize the active ingredient, and degree of therapeutic effect desired. Precise amounts of active ingredient required to be administered depend on the judgement of the practitioner and are peculiar to each individual. Suitable regimes for administration are also variable, but are typified by an initial administration followed by repeated doses at one or more hour intervals by a subsequent administration.

DNA segments (i.e., synthetic oligonucleotides) used to produce a larger DNA segment that comprises the bicistronic coding region of the invention can easily be synthesized by chemical techniques, for example, the phosphotriester method of Matteucci, et al. (J. Am. Chem. Soc., 103:3185–3191, 1981) or using automated synthesis methods. In addition, larger DNA segments can readily be prepared from smaller DNA segments by well known methods, such as synthesis of a group of oligonucleotides that define the DNA segment, followed by hybridization and ligation of oligonucleotides to build the complete segment. The required sequences can also be amplified from native coding regions, for example.

As used herein, the term "vector" refers to a DNA molecule capable of entering and modifying a cell.

The choice of vector comprising a DNA segment of the present invention is dependent on the mode of administration. The vector may be simply naked DNA, a plasmid or a viral vector. The vector may be an "expression vector"—i.e., it may contain control sequences for expression operatively linked to the bicistronic cassette of the invention.

Expression vectors compatible with mammalian cells, and particularly hair follicle cells, are well known in the art and are available from several commercial sources. Typically, such vectors contain convenient restriction sites for insertion of the desired DNA segment, and provide the signals required for gene expression in a mammalian cell. Typical of such vectors are the pREP series vectors and pEBVhis available from Invitrogen (San Diego, Calif.), the vectors pTDT1 (ATCC #31255), pCP1 (ATCC #37351) and pJ4W (ATCC #37720) available from the American Type Culture Collection (ATCC) and the like mammalian expression vectors.

When used in regard to correcting hair pigmentation disorders, particularly preferred are mammalian expression vectors which allow the expression of the gene in a tissue-specific manner, in this case by the action of a regulatory promoter that will limit gene expression to hair follicle cells.

Successfully modified hair follicle cells, i.e., follicle cells that contain the bicistronic cassette of the present invention, can be identified by well known techniques, for example, using a hybridization method such as that described by Southern, *J Mol Biol* (1975) 98:503 or Berent et al. *Biotech* (1985) 3:208.

In addition to directly assaying for the presence of the nucleotide sequence, successful transformation can be confirmed by well known immunological methods for the presence of expressed protein.

Alternatively, successful transformation of the target tissue can be confirmed by evaluation of the target tissue for indicia of function exerted by the administered. For example, where the compound is a nucleic acid expressing tyrosinase, as described in the Examples, the exerted function of pigmentation, or the presence of tyrosinase activity or enzymatic conversion of L-dopa to product can be detected directly in the target tissue.

The following examples are intended to illustrate but not to limit the invention.

EXAMPLE 1

Cloning of the Streptomyces tyrosinase gene, the upstream ORF-438 and the Internal Ribosome Entry Site (IRES)

The sequences encoding the Streptomyces antibioticus tyrosinase gene and ORF-438 were amplified by PCR from plasmid pIJ702 obtained from the American Type Culture Collection (ATCC #35287). Katz, E. et al. J. Gen. Microbiol. (1983) 129:2703–2714.

Oligomers for PCR amplification were designed according to the sequence of *S. antibioticus* tyrosinase gene and ORF-438 cDNA. Bernan, V. et al. Gene, (1985) 37:101–110. In order to enhance expression of the bacterial gene in mammalian cells, the ORF-438 and tyrosinase-gene TGA termination codons were altered to TAA. The Kozak consensus sequence, GCCGCCACC (SEQ ID NO:1), was added upstream, immediately preceding the ATG initiator codon in each case to facilitate translation efficiency.

The sequence of the ORF-438 upstream primer, which included the Kozak consensus sequence was

5'-CGGAATTCGCCGCCACCATGCCGGAACTCACC CGTC-3' (SEQ ID NO:2).

The downstream primer sequence was

5'-GGCTGATCATTAGTTGGAGGGGAAGGGGAGGA GC-3' (SEQ ID NO:3).

The sequence of the tyrosinase upstream primer, which includes the Kozak consensus sequence was

5'-CTCGAGGCCGCCGCCATGACCGTCCGCAAGAA CCA-3' (SEQ ID NO:4).

The downstream primer sequence was

5'-GGATCCTTAGACGTCGAAGGTGTAGTGC-3' (SEQ ID NO:5).

The PCR reaction conditions for both ORF-438 and tyrosinase were as follows: first denaturation at 97° C. for 10 min.; then 10 cycles of denaturation at 97° C. for 30 s; annealing at 66° C. for 30 s; and extension at 72° C. for 45 s; then a final extension at 72° C. for 45 s; then a final extension at 72° C. for 10 min.

PCR oligomers were designed according to the sequence of the internal ribosome entry site (IRES) contained in the retroviral vector pLISN, obtained from Clonetech (Palo Alto, Calif.).

The sequence of the upstream primer was

5'-GGCTGATCATTCGCCCCTCTCCCTCCCC-3' (SEQ ID NO:6).

The downstream primer sequence was

5'-AGCGGCCATTATCATCGTGTTTTCAAAGG-3' (SEQ ID NO:7).

The IRES gene was amplified by PCR from pLXIN as the template. The PCR reaction conditions were as follows: first denaturation at 96° C. for 10 min; then 30 cycles of denaturation at 94° C. for 30 s; annealing at 50° C. for 30 s; and extension at 72° C. for 45 s; then a final extension at 72° C. for 10 min.

Electrophoretic analysis demonstrated that the amplified products had the predicted sizes of 438 bp, 800 bp and 580 bp for ORF-438, tyrosinase and IRES, respectively.

EXAMPLE 2

Retroviral Vector pLmelSN Construction and Packaging

The construction of pLmelSN is shown in FIG. 1. Retroviral vector pLXSN (Clonetech, Palo Alto, Calif.) is a murine leukemia virus-based vector containing two promoters: the 5'-long terminal repeat (5'-LTR) to control the inserted genes and the SV40 promoter to control neomycin phosphotransferase (neoR). The 800-bp tyrosinase PCR product was digested by XhoI and inserted into the HapI/XhoI cloning site of pLXSN to obtain pLtyrSN. The ORF-438 and IRES PCR products were ligated at the Bcl I site and then inserted into the EcoRI/XhoI cloning site of pLtyrSN to obtain pLmelSN. Both the ORF-438 and tyrosinase genes are driven by the Moloney murine leukemia virus 5'-LTR in pLmelSN. See FIG. 1. The bicistronic sequence containing the ORF-438, IRES and tyrosinase genes under control of the 5'-LTR promoter is shown in FIG. 2.

pLmelSN was transfected into the PT67 packaging cell line using lipoTAXI (Clonetech, Palo Alto, Calif.; Stratagene, San Diego, Calif.). The transfected PT67 cell line was selected in DMEM medium containing 0.4 mg/ml G418 (Gibco BRL). The G418-resistant cells were cloned and expanded. After two weeks of selective culturing with G418, positive transfected cells, PT67-mel, were obtained.

EXAMPLE 3

Expression in PT67-mel Cells

In order to confirm the expression of both the ORF-438 and the tyrosinase gene, RT-PCR analysis was used to detect their mRNA in the transfected packaging cells. The RT-PCR products demonstrated that the tyrosinase and ORF-438 genes from *S. antibioticus* were specifically amplified products from the total RNA of pLmelSN-transduced PT7-cells. As a control, mouse 13-actin from both PT67-mel and PT67 cells was amplified by the RT-PCR. Electrophoretic analysis demonstrated that the amplified products from PT67-mel cells had the predicted sizes of 800 bp and 438 bp for tyrosinase and ORF-438, respectively. The RT-PCR reaction with total RNA from uninfected PT67 cells did not amplify these fragments.

In more detail, PT67-mel cells were digested with trypsin and pelleted by centrifugation. Total RNA was extracted by the guanidium thiocyanate method (MicroRNA Reagent Kit, Stratagene, San Diego, Calif.). RNA was quantified by measuring the absorbance at 260 nm. Approximately 10 μg of total RNA was reverse transcribed to first cDNA chains. Reverse transcription was carried out in 20 μl of first-strand buffer, 500 μM of each dNTP, and 20 units of AMV reverse transcriptase (Stratagene, San Diego, Calif.). The PCR primer for the first strand was pORF-438 antisense and pTyr antisense. Samples were incubated at 42° C. for 50 min. The products of the reverse transcription were amplified by the PCR reaction. Mouse β-actin was used as a standard to control the quality of the RNA (Stratagene, San Diego, Calif.).

EXAMPLE 4

Tyrosinase Activity Assay

The transfected packaging cells were screened for the expression of active tyrosinase protein by measuring tyrosinase activity in the lysates of clones of G418-resistant packaging cells. Tyrosinase activity was assessed by the method described by Nakajima et al. *Pigment Cell Res* (1998) 11:12–17. The pLmelSN-infected PT67 packaging cells were plated at a density of 2,000 cells/well in 96 well plates. After 24 hours of culture, the packaging cells were washed with PBS and lysed with 1% Triton-100 (45 μl/well). After mixing the lysates by shaking, 5 μl of 10 mM L-DOPA were added to each well. Following incubation of the culture at 37° C. for 30 min., the absorbance was spectrophotometrically measured at 490 nm.

The DOPA-oxidase reaction was also used to detect melanin production in intact transfected PT67 cells. The cells were incubated with 1 mg/ml of DOPA and 2 mg/ml of tyrosine in PBS (pH 7.4) for 12 hr at 37° C. as previously described. See Kugelman, T. et al. J. Invest Dermatol (1961) 37:66–73.

Figure 3:
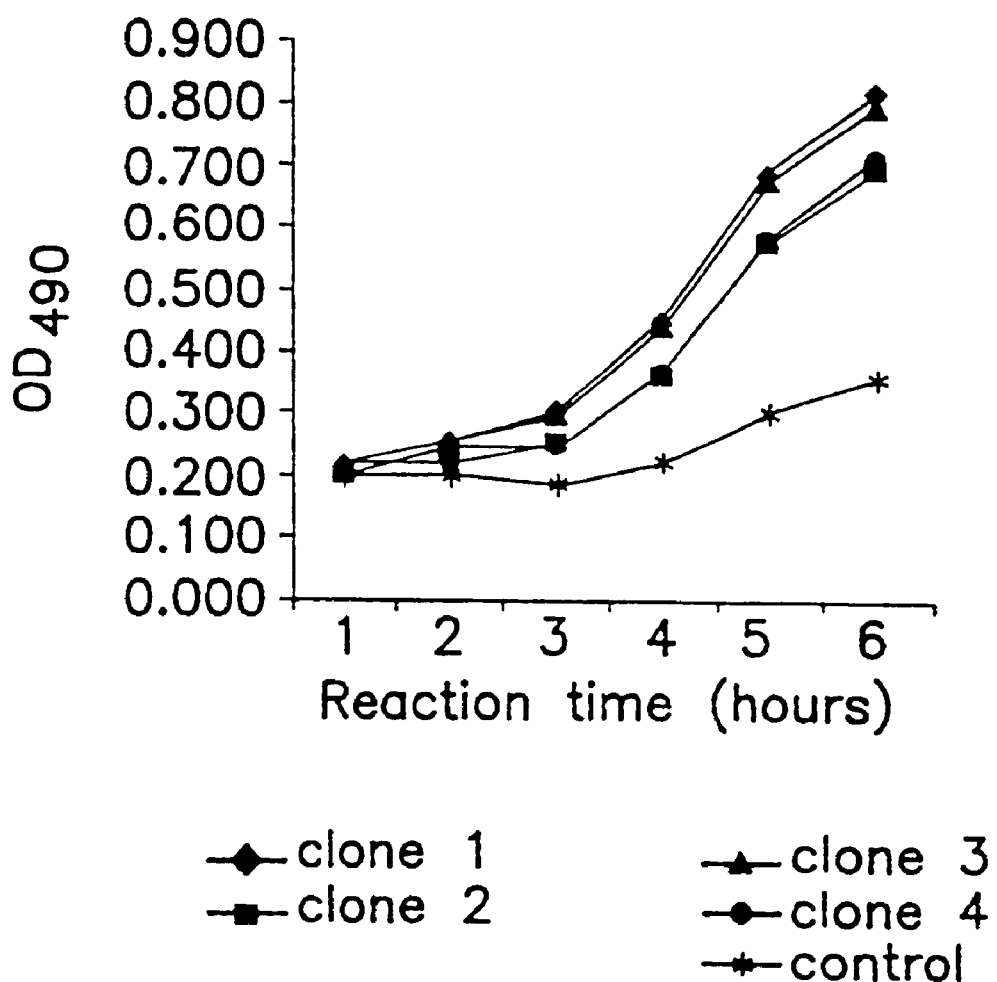
FIG. 3 shows tyrosinase activity in pLmelSN-transduced packaging cells.

Using the same conditions, cell supernatants were measured for melanin content at 490 nm. FIG. 3 shows PT67 clones 1–4 gentrate more melanin than control PT67. The tyrosinase-positive cells were identified by production of brown-colored melanin granules observed with brightfield microscopy. The brown pigment granules were observed only in pLmelSN-transfected cells.

EXAMPLE 5

Retroviral Infection of Amelanotic Melanoma 695T Cells

Human amelanotic melanoma 695T cells (ATCC) were infected for 12 hours with retroviral supernatants containing 8 μg/ml polybrene (Sigma, St. Louis, Mo.). Fresh MEM medium replaced the supernatant. The cultures were then incubated for 48 hours. Cells were then selected in MEM medium containing 0.4 mg/ml G418 for two weeks. Individual clones were isolated and expanded.

Brown melanin pigments were produced in the infected 695T cells. These brown melanin granules could be seen without the DOPA reaction. No pigment granules were seen in the untransduced 695T cells.

EXAMPLE 6

Culture of Albino-Mouse Anagen Hair Follicles

Female albino mice C57BL/6J-Tyrosinase (c-2J), 8 week old, were purchased from the Jackson Laboratory. The growth phase of the hair cycle (anagen) was induced in the back skin, which had all follicles in the resting phase of the hair cycle (telogen). After general anesthesia, a warm wax/rosin mixture was applied and then peeled off the skin, depilating all telogen hair shafts and thereby inducing the follicles to enter anagen. See Schilli *J Invest Dermatol* (1998) 111:598–604.

On day-6 post-depilation, when all hair follicles were in anagen, back skins of the mice were collected after sacrifice.

Small pieces of the mouse skin (2×5×2 mm) were cut with a scissors, and washed three times in HBSS. The harvested skin was incubated at 37° C. in MEM with antibiotics (100 µg gentamycin per ml, 10 µg ciprofroxacin per ml, 2.5 µg amphotericin-B per ml, 100 IU-100 µg penicillin-streptomycin per ml) for 30 min. (Sigma). The skins were washed three times with HBSS medium to remove residual antibiotics and put into collagen-containing gels for histoculture in Eagle's minimum essential medium (MEM) supplemented with 10% fetal bovine serum and gentamycin. Cultures were maintained at 37° C. in a gassed incubator with 5% $CO_2$.

EXAMPLE 7

Infection of Cultured Albino-Mouse Hair Follicles

The histocultured albino-mouse skin of Example 6 was co-cultured with PT67-mel cells as follows:

The PT67-mel cells from the highest producing clone were counted, seeded in 24-well plates, and grown at 37° C. until 80% confluence, and co-cultured with the histocultured albino skin in 24-well plates for 12, 24 and 72 hours. The histocultured skins were then mono-cultured in 24-well plates with fresh MEM medium and incubated for an additional 4–6 days. Small pieces of virus-infected skin were sampled at random. Fresh and frozen sections were prepared by standard techniques.

Melanin was observed in the hair matrix deep in the hair bulbs of the histocultures four days after retroviral infection. Melanin was also found in the upper part of the hair follicles and could be observed in both the hair matrix and hair shaft six days after infection.

In the initial experiments which involved co-culturing histocultured albino mouse skin with PT67-mel cells for 24 hours, approximately 2.5–15% of the skin histocultures contained melanin-producing hair follicles. No melanin was observed in histocultured albino-mouse skin not co-cultured with PT67-mel.

A time-course experiment was then carried out to determine if longer incubation times of the co-cultures of the albino skin and PT67-mel increased the efficiency of tyrosinase infection. The efficiency of infection of the histocultured skin was significantly increased with time of co-culture. After 12 hours co-culture, 7% (2 of 30 pieces) of skin produced melanin, and 15% of hair follicles (6 of 40) produced melanin. After 24 hours co-culture, 25% of skin pieces (5 of 20) produced melanin, as did 35% (28 of 80) of hair follicles. After 72 hours co-culture, 60% of skin pieces (12 of 20) produced melanin as did 53% (42 of 80) of hair follicles.

These results suggest that the virus titer and time exposure to virus can affect the transduction frequency.

Incorporation by Reference

All publications, patents, and patent applications cited herein are expressly incorporated by reference.

What is claimed is:

1. A nucleic acid molecule for efficient production of a functional Streotomyces tyrosinase in mammalian cells comprising a bicistronic nucleotide sequence comprising a first nucleotide sequence encoding said tyrosinase and a second nucleotide sequence encoding ORF-438 coupled through an internal ribosome entry sequence (IRES).

2. The nucleic acid molecule of claim 1 wherein each of said coding sequences is operably linked to a Kozak consensus sequence.

3. The nucleic acid molecule of claim 1 wherein said coding sequences have been modified to contain TAA termination codons.

4. The nucleic acid molecule of claim 1 wherein said coding sequences are operably linked to one or more control sequences that direct expression of said coding sequences.

5. The nucleic acid molecule of claim 4 which is a vector.

6. The nucleic acid molecule of claim 5 which is a viral vector.

7. The nucleic acid molecule of claim 6 which is a retroviral vector.

8. The nucleic acid molecule of claim 7 which is pLmelSN.

9. Isolated hair follicle cells or skin cells transfected with the nucleic acid molecule of claim 1.

10. The cells of claim 9 which are contained in a skin histoculture.

11. The cells of claim 10 which have been synchronized in anagen.

* * * * *